United States Patent [19]

Albert

[11] Patent Number: 4,608,993
[45] Date of Patent: Sep. 2, 1986

[54] BLOOD FLOW MEASUREMENT DEVICE AND METHOD

[75] Inventor: David E. Albert, McAlester, Okla.

[73] Assignee: Quinton Instrument Company, Seattle, Wash.

[21] Appl. No.: 636,383

[22] Filed: Jul. 31, 1984

[51] Int. Cl.$^4$ .............................................. A61B 10/00
[52] U.S. Cl. .................... 128/663; 73/861.25
[58] Field of Search ............... 128/660, 661, 663, 713, 128/715; 73/861.25

[56] References Cited

U.S. PATENT DOCUMENTS

| | | | |
|---|---|---|---|
| 4,152,928 | 5/1979 | Roberts | 128/663 |
| 4,205,687 | 6/1980 | White et al. | 128/663 |
| 4,255,977 | 3/1981 | Newhouse et al. | 128/663 |
| 4,391,148 | 7/1983 | Sainz et al. | 73/861.25 |
| 4,413,531 | 11/1983 | Karplus et al. | 73/861.25 |
| 4,434,669 | 3/1984 | Roberts et al. | 128/663 |

FOREIGN PATENT DOCUMENTS 0573152  9/1977  U.S.S.R. ............................... 128/661

OTHER PUBLICATIONS

Sainz et al, "A New Approach to Doppler Ultrasound Flowmetry", Conference: Ultrasonics International, 1977, Brighton, England (28–30, Jun. 1977) pp. 214–220.
Callicot et al, "A Maximum Frequency Detector for Doppler Blood Velocimeters", Journal of Medical Eng. and Technology, vol. 3, No. 2, Mar. 1979, pp. 80–82.
Coghlan et al, "Improved Real-Time Spectrum Analyser for Doppler-Shift Blood Velocity Waveforms", Medical & Biological Engineering and Computing, May 1979, vol. 17, No. 3, pp. 316–322.
McCarty, "Frequency Modulated Ultrasonic Doppler Flowmeter", Medical and Biological Engineering, vol. 13, No. 1, Jan. 1975, pp. 59–64.
Gerzberg et al, "Power Spectrum Centroid Detection for Doppler Systems Applications", Ultrasonic Imaging, vol. 2, No. 3, Jul. 1980, pp. 232–258.
Skidmore et al, "Maximum Frequency Follower for the Processing of Ultrasonic Doppler Shift Signals", Ultrasound in Med. & Biol., vol. 4, No. 2, 1978, pp. 145–147.
Thomson, "Broadband Pulsed Doppler Ultrasonic System for the Non-Invasive Measurement of Blood Velocity in Large Vessels", Medical & Biol. Eng. & Computing, Mar. 1978, vol. 16, No. 2, pp. 135–146.
Peeters et al, "A Self-Correcting, Phase-Locked Tracking Method for Pulsed Ultrasound", IEEE Transactions on Biomedical Engineering, vol. 26, No. 2, Feb. 1979, pp. 119–122.

Primary Examiner—Kyle L. Howell
Assistant Examiner—Ruth S. Smith
Attorney, Agent, or Firm—Burns, Doane, Swecker & Mathis

[57] ABSTRACT

The disclosure relates to systems for measuring blood flow by detecting Doppler shift of ultrasound reflected by blood components moving in a blood vessel. The systems employ electronic techniques for providing accurate tracking of portions of the frequency spectra of Doppler shift signals to determine peak and means velocity and acceleration.

27 Claims, 19 Drawing Figures

BLOOD FLOW MEASUREMENT DEVICE AND METHOD

BACKGROUND OF INVENTION

1. Field of the Invention

The present invention concerns a blood velocity and acceleration measurement system. More particularly, it concerns an improved, non-invasive blood velocity and acceleration measurement device based on the use of Doppler ultrasound, and capable of providing measurements of peak velocity and peak acceleration of blood components, as well as a mean velocity and acceleration thereof. In addition, a method and apparatus for calibrating the blood flow measurement devices are disclosed.

2. Brief Discussion of Prior Art

Velocity and acceleration of blood flow in blood vessels are believed to be an important diagnostic tool. In particular, the peak acceleration of aortic blood flow has been recognized to be an excellent index of ventricular function. "A substantial body of evidence indicates that the peak acceleration of the blood corpuscles ejected by the left ventricle into the ascending aorta is the most sensitive indicator of ventricular performance" Rushmer, *Cardiovascular Dynamics*, p. 365 (4th ed. 1976). Rushmer's conclusion is that the acceleration of blood corpuscles in the aorta would be a valuable index of the influence on cardiac function of various perturbations, e.g., such as coronary occlusion, exercise, and drug infusion—a conclusion which Rushmer demonstrated experimentally. Other observers have considered peak acceleration, peak velocity, mean velocity, and mean acceleration of the blood corpuscles to be useful indices of cardiac performance.

There is a recognized need for a non-invasive indicator of ventricular performance that can provide ready access to reliable data regarding critical variables or parameters of cardiac performance. ("Invasive" techniques are those involving physical penetration of the body, such as by surgical opening of a portion of the body to permit insertion of a measurement device, or by injection of dyes to permit X-ray visualization.)

Recognized authorities have stated that it is not possible to measure aortic blood flow acceleration non-invasively. See Gams, Huntsman, and Chimoskey, *Peak Aortic and Carotid Flow Acceleration in Trained Unanesthetized Dogs*, Federation Proceedings, American Physiological Soc'y (1973). A prevalent technique presently used for evaluating cardiac performance in human patients is the radioisotope ventriculogram procedure. However, the necessary equipment is extremely expensive; specifically trained and licensed technicians are needed; and the tests involve insertion of a catheter into the patient's vein. Other invasive techniques are available in the case of animal experimentation, but the techniques are usually unsatisfactory for human patients. For example, some experimenters have inserted measuring devices into or adjacent to the aortas of laboratory dogs and humans. In the past, such invasive techniques have been used to strengthen medical understanding of blood flow. Although they are helpful for research purposes, such invasive techniques are usually not clinically practical or create risks to the patient.

Doppler ultrasound is used as a clinical and research tool in the evaluation of blood circulatory dynamics. The use of Doppler ultrasound may involve determining the speed of a reflecting material by beaming ultrasonic waves at the object and then measuring the frequency shift in the ultrasound waves reflected by the material.

Experimental work has indicated that ultrasound signals for blood velocity measurement can conveniently be transmitted into the body via the suprasternal notch, thereby facilitating evaluation of the ascending aortic or distal aortic arch blood flow. This "acoustic window" (as we may term the place via which ultrasound is beamed into the body) may be used in many types of patients.

Presently available electronic circuitry for decoding Doppler shift signals for blood flowmeter purpose generally use the "zero-crossing detector" method of determining Doppler shift frequencies. This is the method used, for example, in White U.S. Pat. No. 4,205,687. The method develops an RMS value of frequency which is not directly indicative of peak or mean velocity or acceleration. As shown by Lunt in his paper *Accuracy and Limitations of the Ultrasonic Doppler Blood Velocimeter* in *Ultrasound in Medicine & Biology*, 2:1–10 (1975), it is hard to achieve accurate blood velocity measurements with the zero-crossing detector method.

Techniques commonly in use for detection of peak Doppler frequencies present various problems. The fast Fourier transform ("FFT") technique requires expensive and elaborate equipment, and presently known FFT systems are not fast enough to measure peak acceleration. Other known peak frequency detection systems, such as voltage-controlled high pass filters, phase-lock loop systems, and double filters are noise sensitive, have a limited band width and frequency response, and are sensitive to amplitude modulation ("AM") of the signal.

Skidmore and Follett, in *Ultrasound in Med. & Biol.*, 4:145 (1978), suggest Doppler-shift measurement of blood velocity. They suggest detection of maximum Doppler frequency by use of a voltage controlled high pass filter. But their system has not been put into commercial use. It is believed that the reason is that it is too sensitive to noise. Also, it appears not to be able to measure the frequencies associated with the highest velocity corpuscles, which are considered of greatest interest.

Callicot and Lunt, in "A maximum frequency detector for Doppler blood velocimeters", *J. Med. Engineering & Technology* 3:80 (1979), note the use of phased lock loop techniques to measure peak velocity and mean velocity, and disclose a system in which a voltage controlled oscillator in a feedback loop is used to detect maximum frequencies representative of blood corpuscle velocities. Callicot et al does not show tracking of the high frequency edge of the frequency spectrum. FIG. 2 of the article illustrates this in that it shows that the system significantly underestimates the true peak velocity as measured by the sonagram. The slope of the velocity is not tracked. The system cannot respond rapidly enough to accurately detect peak acceleration. Moreover the system cannot measure peak velocity as shown by their illustrations. Neither Skidmore and Follett's or Callicot and Lunt's circuit has sufficient frequency response to accurately measure peak aortic acceleration.

There, thus, exists a need for a non-invasive technique for measurement of peak aortic acceleration. The need could be satisfied by a Doppler ultrasound device, if one could be devised (a) that was relatively inexpensive, noise-free, and insensitive to AM, and (b) that had a sufficient bandwidth and frequency response to register higher Doppler frequencies and rate of change of frequencies. It is believed by the inventor that the need for a non-invasive technique is well recognized in the art, and that other workers have sought to satisfy this need by a Doppler type device. The inventor does not believe that it is recognized in the art that the above-stated requirements must be met for a satisfactory Doppler ultrasound system. In any event, no such satisfactory Doppler system known to the inventor is presently available. The present invention concerns such a system: a real-time Doppler ultrasound, non-invasive system for measuring peak aortic (or other vessel) acceleration and velocity, which is relatively inexpensive, noise free, insensitive to AM, and with band width and frequency response sufficient to track high velocity, high acceleration blood component movement. Moreover, there is a need for non-invasive techniques for accurately and inexpensively determining mean blood velocity and acceleration.

These needs are realized by the techniques disclosed as follows.

BRIEF SUMMARY OF THE INVENTION

The invention described below is intended to provide an accurate real-time Doppler ultrasound system for measuring peak and mean velocity and acceleration in blood flow. The system may be employed to track the leading edge of the Doppler spectrum. The leading edge or highest-frequency part of the Doppler spectrum may be detected by circuitry which includes an automatic gain control circuit and a tracking circuit.

The tracking circuit may include a mixer for modulating the audio frequency Doppler shift signal up to a frequency greater than 100 kHz. The modulated signal may then be applied to a high Q, fixed frequency band pass filter. The filtered signal may then be used to control a local oscillator which provides a carrier signal. The carrier signal is mixed with the Doppler shift signal in the mixer. The feedback signal which controls the local oscillator is representative in value to the instantaneous peak velocity of reflecting components in the blood flow.

Accordingly, a signal can be developed that is representative of the highest frequency in the Doppler spectrum, and thus is representative of peak velocity in blood flow. Differentiation of the peak instantaneous velocity signal provides a signal related in value to the peak instantaneous acceleration. The peak value of this signal for a single heartbeat may be derived as an indication of cardiac function.

Another implementation of the circuitry uses the difference between the outputs of voltage controlled high- and low-pass filters to vary the cut-off frequencies of the same filters, so that the system tracks the mean-frequency of the Doppler shift signal rather than the peak frequency.

An automatic gain control (AGC) circuit is provided for the Doppler shift signal. The overall power in the spectrum of the Doppler shift signal will be different at different times during a single heartbeat. To improve the accuracy of the mean and peak velocity and acceleration detection circuits, the overall instantaneous power of the spectrum may be maintained approximately constant by the AGC circuit. The gain control circuit allows the mean or peak velocity tracking loops described above to follow more faithfully frequency changes in the Doppler signal, by minimizing the effects of amplitude change and inhibiting amplification of noise. In preferred embodiments, the gain control circuit includes a local oscillator for producing a low audio frequency sinusoidal signal, for example at 440 HZ, which is summed with the Doppler shift signal. The amplitude of the summed signal is maintained approximately constant by a fast acting AGC circuit.

A calibration circuit is also provided for embodiments of the present invention. The calibration circuit produces band-limited white noise which simulates the instantaneous Doppler spectrum for calibration purposes.

BRIEF DESCRIPTION OF THE DRAWINGS

FIG. 3b is a graph of peak frequency shift during a heart beat, plotted on the same time scale as FIG. 3a.

FIGS. 5a–c are graphs of various signals appearing at point "A" in FIG. 4.

DETAILED DESCRIPTION

The present invention relates to a non-invasive, ultrasound hemodynamic monitor system. The achievement of highly accurate, real time measurement of peak and mean blood flow velocity and acceleration with a non-invasive probe permits the system to be used in monitoring patients in clinical situations. It is contemplated that the system may be used for the following more specific purposes, among others: measuring blood perfusion to specific vessels, ambulatory monitoring of patients, monitoring of patients in standard treadmill exercise tests, monitoring by paramedic or emergency mobile units (with or without telemetry); anesthesiology monitoring in operating rooms; and evaluation of cardiac function in patients receiving cardiotoxic chemotherapy.

Figure 1:
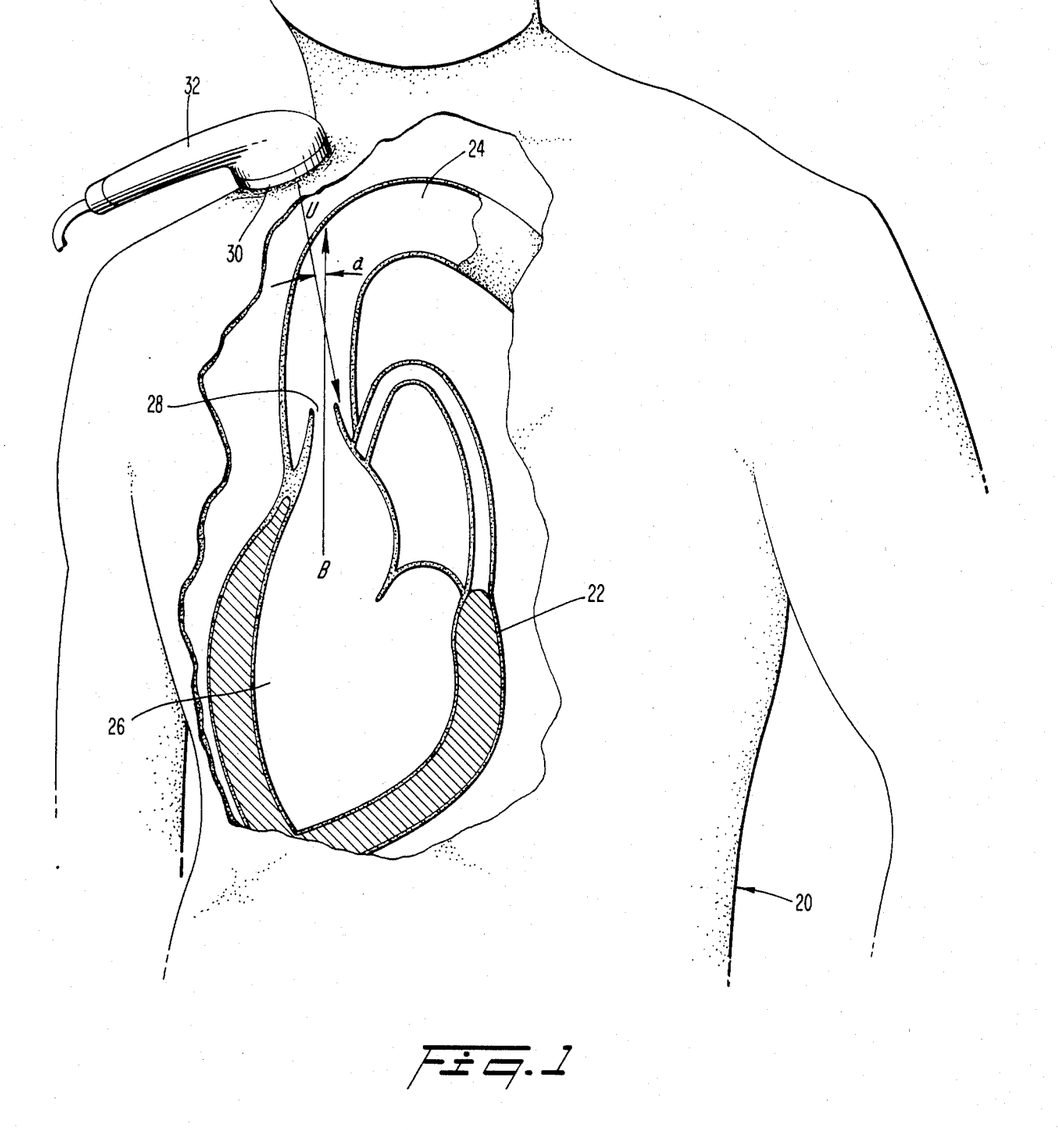
FIG. 1 is a vertical cross-sectional view of the aorta and left ventricle of a human being, showing an ultrasonic transducer apparatus placed on the suprasternal notch and directed toward the ascending aorta.

The non-invasive probing techniques for obtaining Doppler shift signals are illustrated in FIG. 1. In FIG. 1, a portion of the human body is indicated generally by the numeral 20. The chest of the body is shown in cross-section as is the heart 22 and aorta 24. Arrow B represents the flow vector of blood exiting the left ventricle 26 through the aortic valve 28. It is the parameters of this blood flow which are the subject of measurement. However, as will be clear from the following, the techniques described herein may be adapted to measuring blood flow parameters in other blood vessels.

Non-invasive probing of blood flow in the aorta 24 may be achieved by directing a beam of ultrasonic energy U into the aorta and measuring the Doppler shift of reflections from moving blood components in the aorta. Those blood components providing usable reflection may be the red blood cells or erythrocytes. Ultrasonic energy may be directed and returned through the suprasternal notch 30, which is an acoustic window of the body through which ultrasonic energy will pass relatively unattenuated. A transducer apparatus 32 may be employed to direct the ultrasonic energy into the body and receive reflected ultrasonic energy.

It has been found (see, e.g., Papadofrangakis U.S. Pat. No. 4,265,126; and Aronson U.S. Pat. No. 4,103,679) that blood velocity may be measured by the Doppler shift in accordance with a relatively simple equation:

$$V = SD/2T \cos a$$

Where:
V = velocity of blood corpuscles;
S = velocity of ultrasound in tissue (1540 meters per sec);
D = Doppler frequency shift;
T = Transmitted ultrasound frequency;
a = angle between the blood velocity vector and the sonic vector from the ultrasound transducer.

In their paper, *Continuous Wave Ultrasonic Doppler for Measuring Aortic Velocity and Acceleration* (U. Wash., Center for Bioengineering, 1977), Johnson, Fairbanks, and Huntsman indicate that the mean value of angle a, when the suprasternal notch is used as the acoustic window and the ascending aorta is the target, is about 6°. The cosine of 6° is very close to 1.00. Hence, the cos a term of Equation (1) is unimportant, whether or not there are variations in angle, and the cosine term of the equation therefore may be ignored. This obviates recourse to the expedients discussed, for example, in Hassler U.S. Pat. No. 4,127,842. This also leads to a simplified version of Equation (1):

$$V = SD/2T.$$

Figures 2, 5:
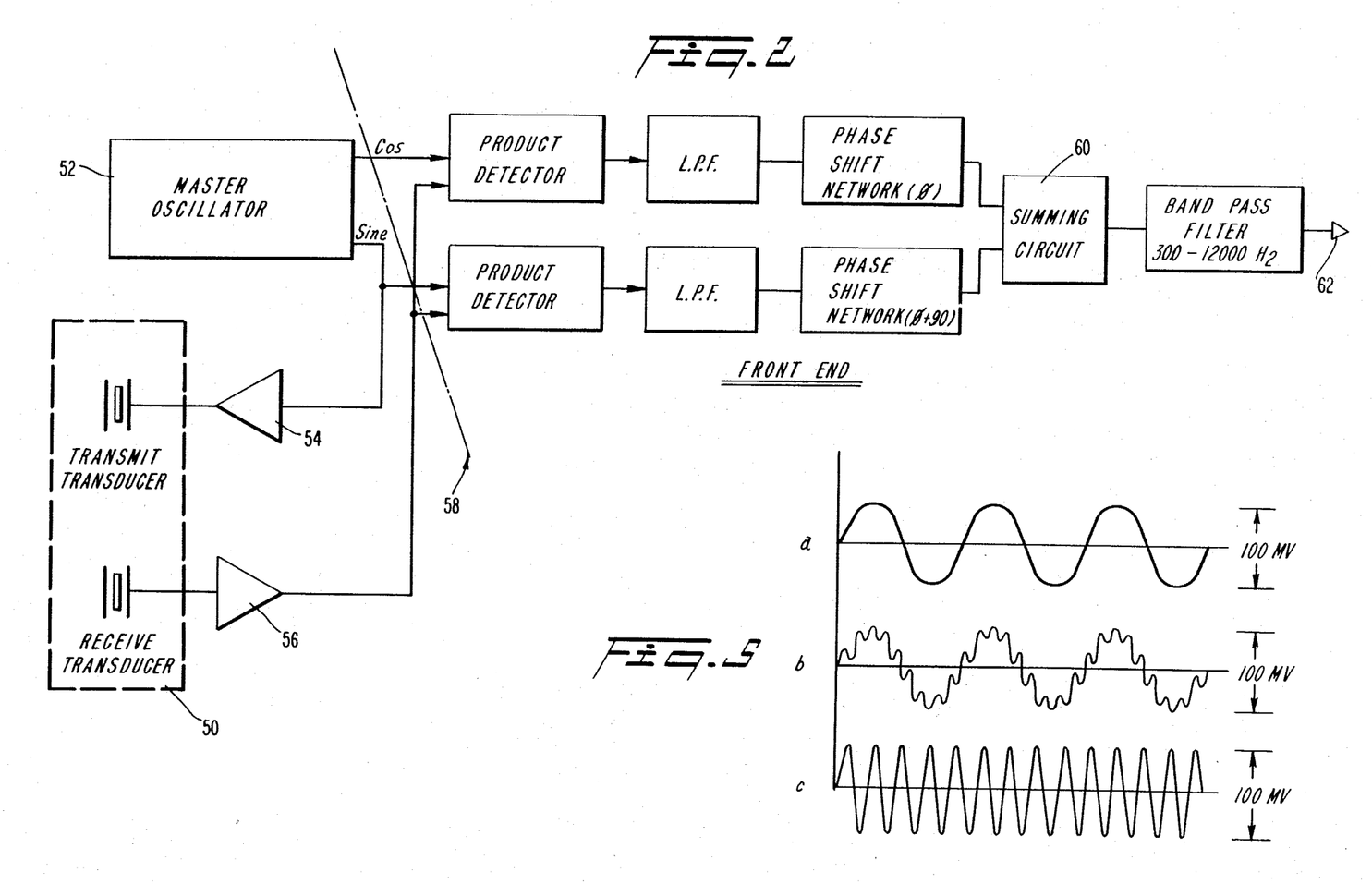
FIG. 2 is a schematic block diagram of a front end portion of a continuous wave, directional blood flow measurement circuit.

FIG. 2 is a block diagram of a front end portion of a blood flow measurement system constructed in accordance with the teachings of the present invention. Transmitting and receiving transducers 50 may be provided and located in a hand held probe such as the device 32 shown in FIG. 1. A master oscillator 52 may provide an ultrasonic signal (e.g., 2–10 MHz) which is amplified by amplifier 54 and applied to the transmitting transducer. Reflected ultrasonic energy is detected by the receiving transducer and may be amplified by amplifier 56.

The circuitry shown on the right side of line 58 in FIG. 2 is a circuit for electronically extracting audio frequency Doppler shift signals. The system employs a conventional quadrature detection technique employing pairs of product detectors, low pass filters and phase shift networks. An audio frequency Doppler shift signal is produced at the output of the summing circuit 60. This signal is applied to a band pass filter which band limits the Doppler shift signal to a band ranging from about 100 Hz to about 10 kHz. In a preferred embodiment, this band ranges from 300 Hz to 12,000 Hz. The parameters of the band are dictated at the lower end by a need to filter out low frequency sound produced by the heart itself and by blood vessel vibration. At the upper end, the frequency cut off is selected so that the band is wide enough to include the highest detectable Doppler shifts encountered in the reflection of the ultrasonic energy from the blood components.

The band limited audio frequency shift Doppler shift signal appears at terminal 62 and is applied to further processing circuitry which will be described below.

The signal appearing at terminal 62 will now be described in connection with FIGS. 3a through 3d.

It will be apparent that blood velocity and acceleration varies with time during a single heart beat. Accordingly, the Doppler shift of the ultrasonic signals will vary with time during the heartbeat. In addition, moving blood components from which reflections are obtained will differ in velocity due to the fluid dynamic properties of the blood, e.g., streamlining and boundary layering. This results in a spectrum of Doppler shift frequencies, at any given instant rather than a single spectral line. Doppler shift spectra are graphed in three dimensions in FIG. 3a, to show variations of power and frequency with time.

Several salient features of the plot of FIG. 3a will now be discussed. The line 80 represents the leading or high frequency edge of the Doppler shift signal. This line corresponds to the highest frequency at any given point of time which is detectable above the noise level of the system. The upwardly inclined portion 82 of line 80 represents the onset of systole. A lower line 84 represents the lower limit frequency cut-off of the signal at about 100 Hz–300 Hz.

Figure 3A:
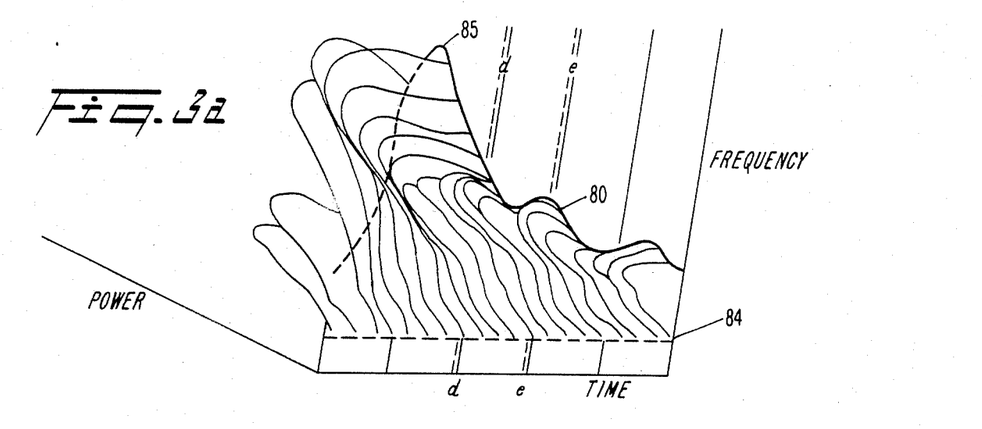
FIG. 3a is a three dimensional projection of Doppler shift spectra showing the changes in the spectra with time corresponding to blood velocity changes during a heart beat.
Figure 3B:
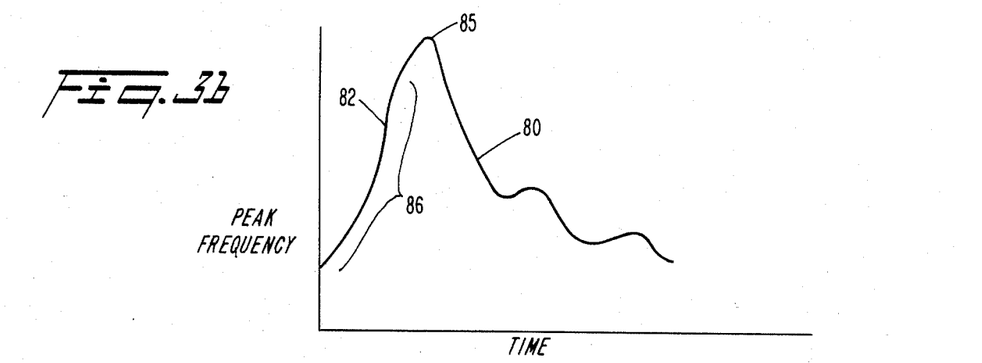

FIG. 3b is a two-dimensional graph of peak Doppler shift frequency with respect to time. It will be readily understood that the peak frequency represented by line 80 is an analogue of the instantaneous velocity of the fastest blood components as a function of time. Point 85 represents the peak velocity achieved during a single heart beat. The steep portion 86 of the curve 80 represents a rapid increase in the instantaneous peak frequency, hence in the instantaneous peak velocity, of the blood during the onset of systole. The curve is steepest at the point of peak acceleration. The frequency value of the audio Doppler shift in the region 86 may be approximately 1000 to 1500 Hz for a normal heartbeat with the body at rest.

Figure 3C:
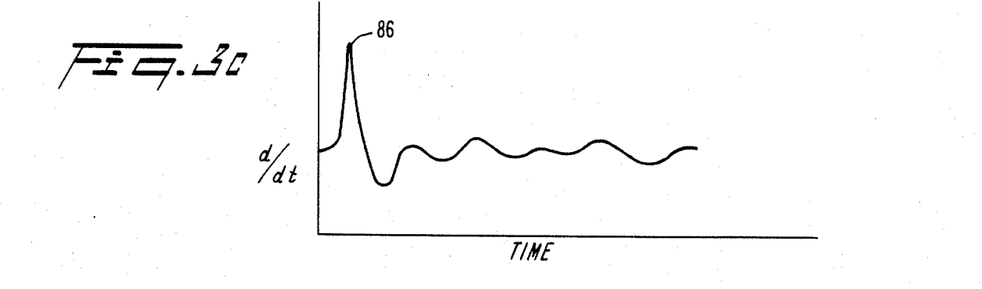
FIG. 3c is a graph of the first time derivative of the function shown in FIG. 3b.

FIG. 3c is a plot representing the time differentiation of the function of curve 80. It will be readily appreciated that this plot represents the instantaneous peak acceleration of the blood components as a function of time. The point of peak acceleration during a single heartbeat is represented by the point 86. It should be noted that point 86 is preceded and followed by extremely rapid rates of change in the acceleration. This extremely rapid rate of change is difficult to track and probably accounts for the failure of the prior art to teach a workable system for detecting peak velocity and acceleration. As used herein, the terms "velocity" and "acceleration" are used in their generic sense without limitation to the direction, i.e. acceleration is used synonymously with both positive acceleration and deceleration; velocity is used to connote speed both toward and away from the receiving transducer.

Figure 3D:
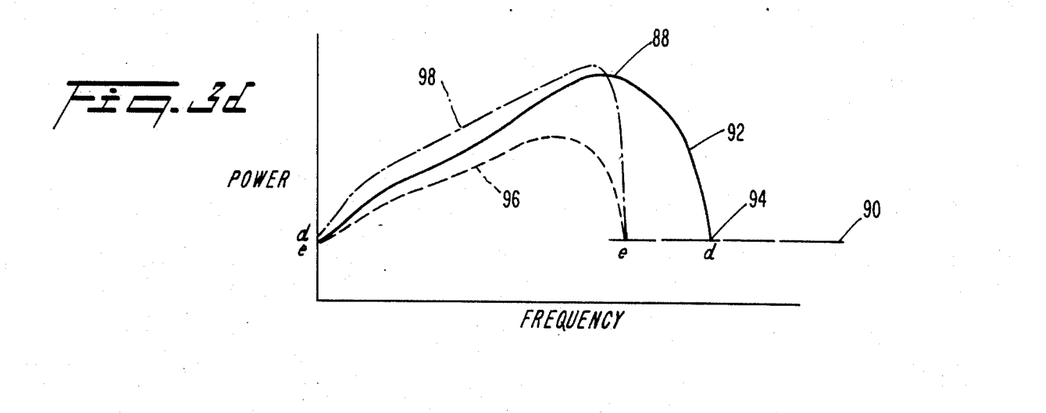
FIG. 3d is a graph of the frequency spectra of Doppler shift signals at times d—d and e—e.

FIG. 3d is a plot of the power spectrum of the Doppler frequency shifts occurring at an instant of time denominated by the line d—d in FIG. 3a. It will be readily understood that the point 88 corresponds to the instantaneous mean velocity of the reflecting blood components at the instant d—d. The line 90 reflects the noise of the system. It has been observed emperically that the frequency spectrum envelope 92 shown in FIG. 3d rolls off rapidly at higher frequencies. This roll-off corresponds approximately, to a 4th order low pass filter or approximately 40 dB per decade roll-off. Accordingly, the magnitude of the noise level 90, available with state of the art components, does not mask the leading edge and, thus, the peak frequencies of the Doppler spectrum.

Figure 4:
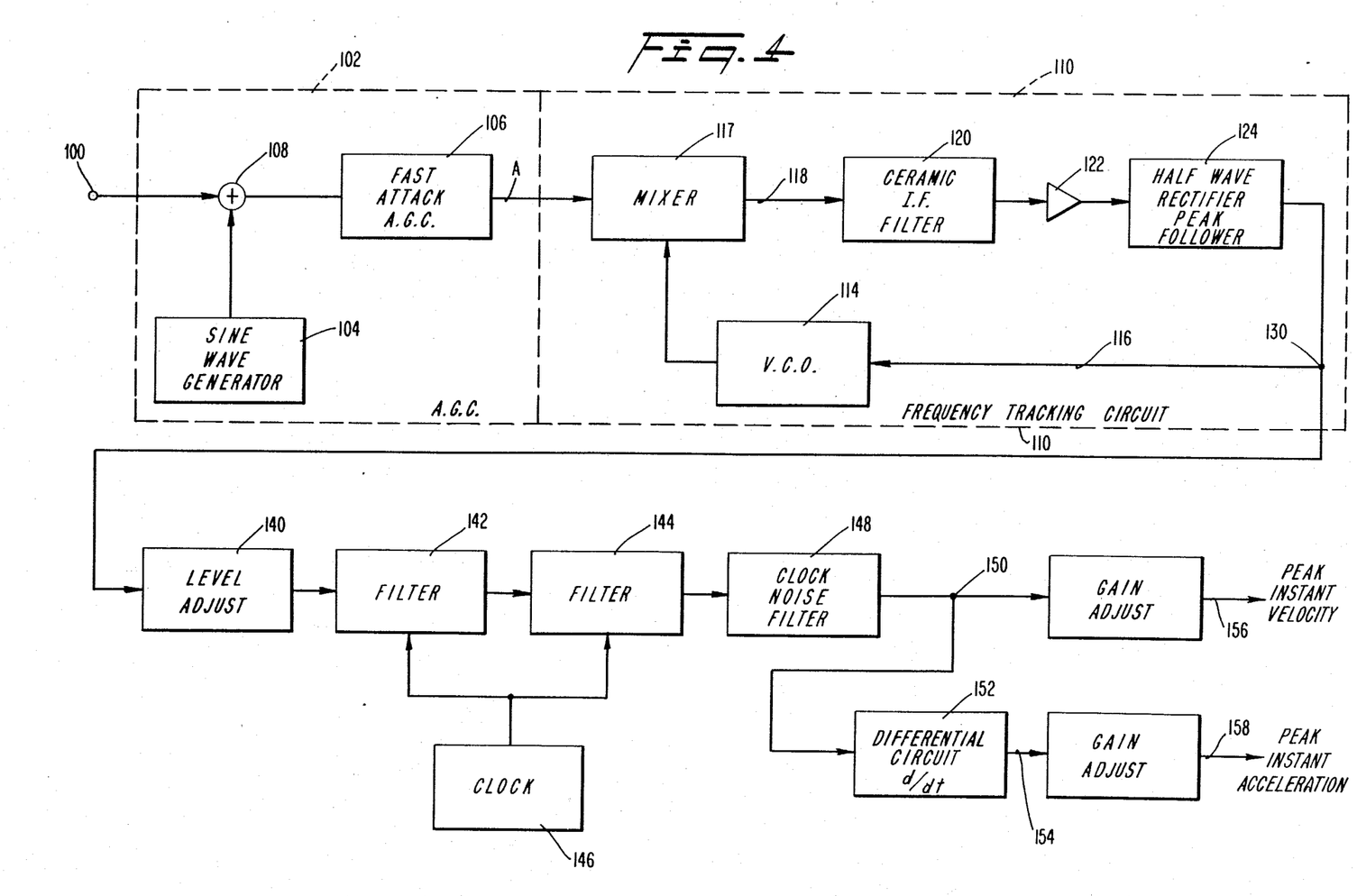
FIG. 4 is a schematic block diagram of a circuit for determining peak velocity and peak acceleration from a Doppler shifted ultrasonic signal.

Referring next to FIG. 4 a schematic block diagram is shown for a circuit for determining peak velocity and peak acceleration from a Doppler shifted ultrasonic signal. An input terminal 100 of the circuit of FIG. 4 may be connected to the output terminal 62 of the front end circuit shown in FIG. 2. That signal is applied to an AGC circuit 102.

The AGC circuit 102 may include a sine wave generator 104 and a a fast attack AGC circuit 106. The Doppler shifted audio signal (discussed in connection with FIG. 3) is summed with a sinusoidal signal from the sine wave generator at a summing circuit 108.

The frequency at which the sine wave generator 104 is operated, is selected to be low enough so as not to obscure important information bearing frequency bands in the Doppler shift signal. The frequency may be selected to be less than 1000 Hz and in a preferred embodiment, is selected as 440 Hz. The fast attack AGC circuit 106 operates to maintain the peak to peak amplitude of the summed signal at an approximately constant value.

The operation of the AGC circuit is best illustrated in connection with FIGS. 5 which show various signals appearing at node A in the circuit of FIG. 4. FIG. 5a illustrates the signal at node A when no Doppler shift signal is being applied to terminal 100. This signal is a replica of the sinusoidal signal from the sine wave generator. In FIGS. 5b and c progressively larger Doppler shift signals are applied at terminal 100 and summed at circuit 108. It should be noted that the wave forms illustrated in Figures a, b and c have substantially identical peak to peak values (e.g. 100 millivolts). This effect is achieved by the fast attack AGC circuit 106.

The AGC circuit 102 operates to normalize the power in the Doppler shift frequency spectrum while preserving the relative frequency distribution within the spectrum.

The effect of the automatic gain control circuit may be best illustrated with reference to FIG. 3d. FIG. 3d illustrates a plot 96 of power vs. frequency such as might occur at the instant of time indicated as e—e in FIG. 3a. This signal would be applied to terminal 100 of the automatic gain control circuit. As is apparent from the figure, the total power in the spectrum 96 is significantly less than the power in the spectrum 92. The automatic gain control circuit tends to normalize the power in the various spectra during a heartbeat. Thus, the power levels of spectrum 96 would be increased so that the spectrum 98 would be applied at node A. However, the gain control function does not significantly distort the frequency distribution or general shape of the Doppler shift spectra.

The automatic gain control circuit also operates to prevent the amplification of unwanted higher frequency noise components when smaller amplitude signals are detected in the system. It will be understood that when substantially no Doppler shift signal is present at terminal 100, the wave form appearing at A will be substantially as shown in FIG. 5a. This non-information bearing sine wave signal will be filtered out in the subsequent circuitry.

Figure 8:
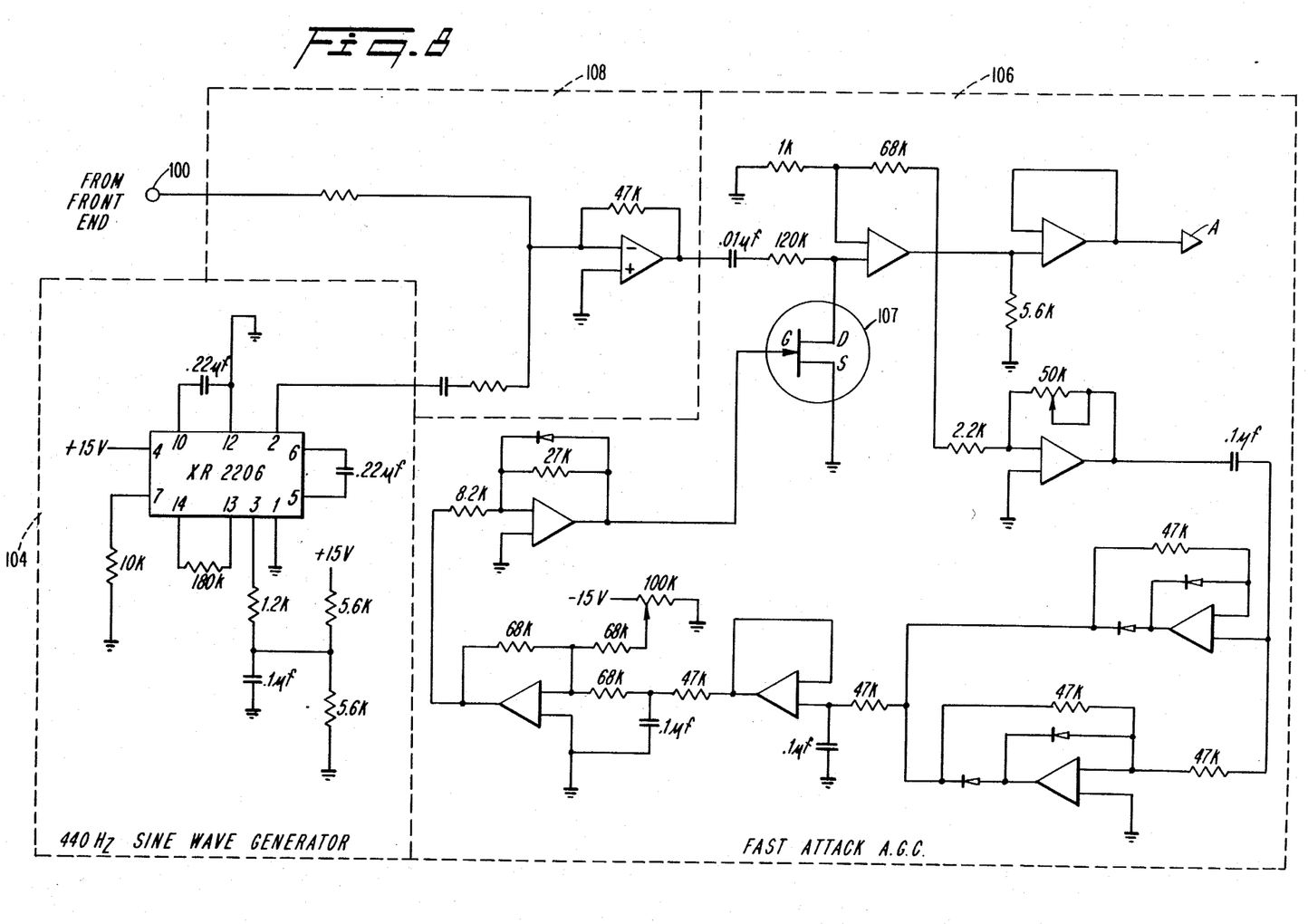
FIG. 8 is a schematic circuit diagram of a gain control portion of a blood flow measurement circuit.

A circuit implementing the design of the automatic gain control system illustrated in FIG. 4 is shown in FIG. 8, wherein like components and features are identified with like numerals. The circuit of FIG. 8 employs an XR2206 integrated circuit manufactured by EXAR to generate a 440 Hz sine wave signal which is summed at summing circuit 108. The fast attack AGC circuit is of conventional design employing a feed back controlled field effect transistor 107.

With continued reference to FIG. 4, a frequency tracking circuit 110 of the present invention will now be discussed. The gain controlled Doppler shifted audio signal at A is applied to a mixer 112 where it is mixed with a carrier signal produced by a local oscillator 114. The local oscillator 114 is operated at a frequency in excess of 100 kHz. The operation of the mixer is to modulate or heterodyne the Doppler shift signal up to a much higher frequency which is more readily filtered by a band pass filter. The frequency of oscillation of the local oscillator 114 is controlled by a feedback loop 116 so that the circuit tracks the leading or high frequency edge of the Doppler shifted signal.

The signal appearing at the output terminal 118 of the mixer 112 may be the upper or sum side band of the two signals. The carrier or local oscillator frequency and the lower side band may be suppressed. The signal from the mixer is applied to a high Q band pass filter such as a ceramic IF filter having a Q greater than about 100. In a preferred embodiment of the present invention, the filter employed is a ceramic filter manufactured by the Murata Company designated as CFU455H. The filter has a center band pass frequency of 455 kHz. In this system, the quiescent frequency of the local oscillator 114 is likewise selected to be 455 kHz.

An output signal from the band pass filter 120 may then be applied to an amplification circuit 122. The amplified output from the amplifier 122 may then be applied to a halfwave rectifier and peak follower circuit 124.

Figure 6A:
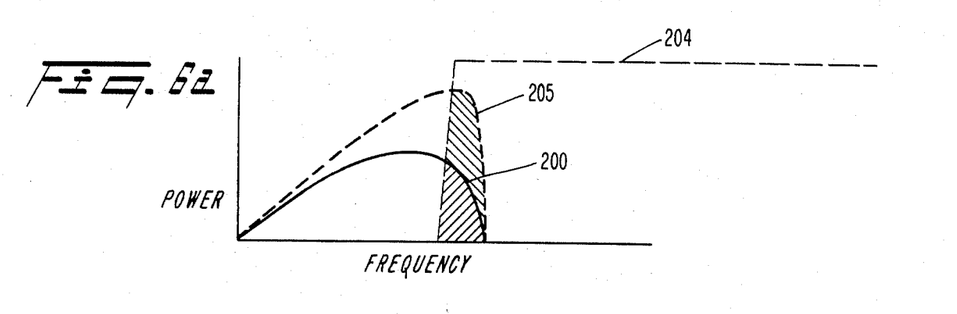
FIGS. 6a & 6b and 7a & 7b are graphs of instantaneous frequency spectra of Doppler shifted signals showing various filter cut-off profiles.
Figure 9:
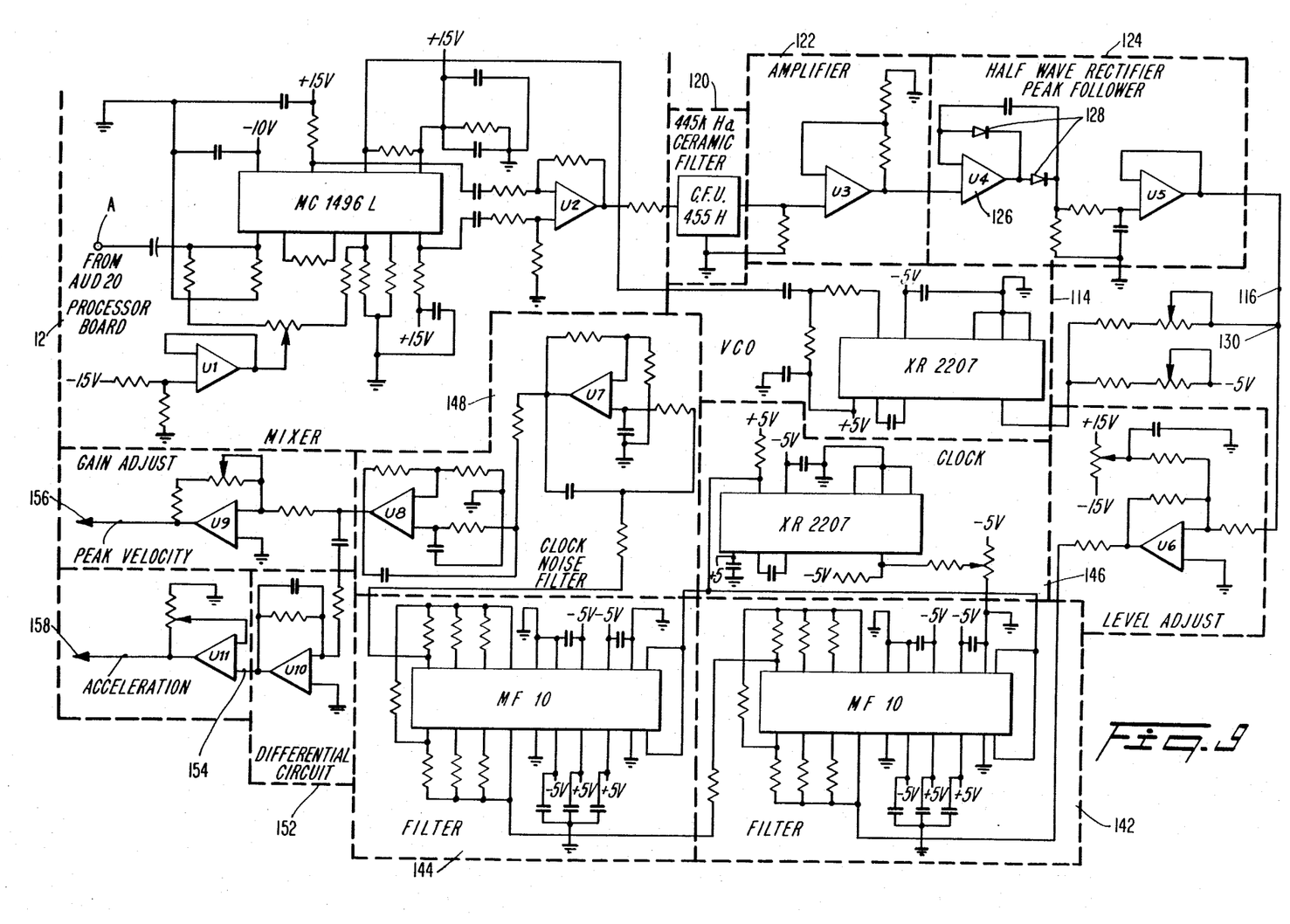
FIG. 9 is a schematic circuit diagram of a filter and signal processing portion of a blood flow measurement circuit for determining peak velocity and peak acceleration from a Doppler shifted ultrasonic signal.

A circuit implementation of the frequency tracking circuit 110 shown in block form in FIG. 4 is illustrated in FIG. 9, wherein like features and components are identified with like numerals. In the circuit embodiment shown in FIG. 9, the Doppler spectrum at node A is modulated up to 455 kHz in an interated circuit mixer identified as MC1496L manufactured by Motorola Company. A nominal 455 kHz signal is generated by a voltage controlled oscillator (VCO) 114 based on an integrated circuit identified as XR2207 manufactured by EXAR. The feed back loop 116 is designed to maintain the energy overlap between the filter and the Doppler spectrum constant by changing the VCO beat frequency. As the sectral components of the Doppler shift signal increase in frequency with the acceleration of blood, the feedback loop acts to decrease the VCO frequency thereby lowering the spectrum of the upper side band down from the 455 kHz pass band of the ceramic filter 120. When no Doppler signal is applied at A, the VCO is operated at a quiescent frequency of 455 kHz. As the spectrum increases in frequency, the VCO compensates by decreasing the frequency of its output signal, thereby keeping the energy integral of the spectrum within the filter profile at an approximately constant level. This effect is best illustrated with reference to FIGS. 6 and 7. FIG. 6a illustrates a plot 200 of power vs. frequency in a Doppler shifted signal such as would appear at A. As blood velocity increases during the onset of systole, the Doppler shift spectrum shifts to higher frequencies as illustrated by the plot 202 in FIG. 6b. The dotted lines 204 illustrate the steep filtering characteristics or profile of the circuit of the present system.

Figure 6B:
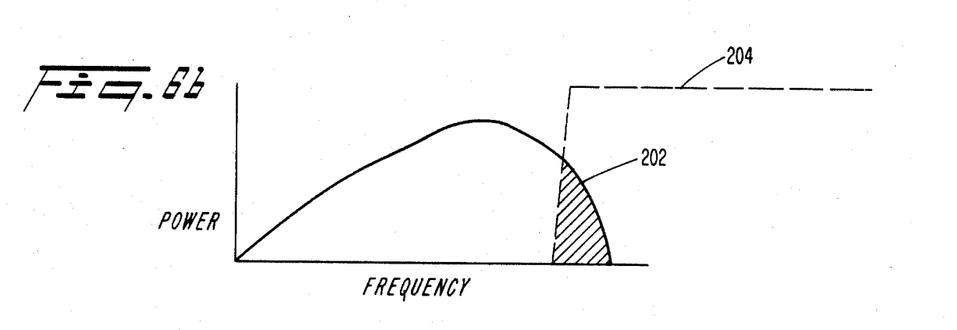
Figure 7A:
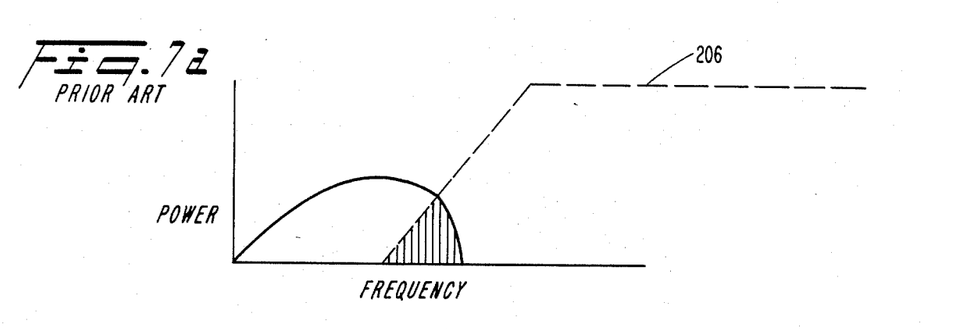
Figure 7B:
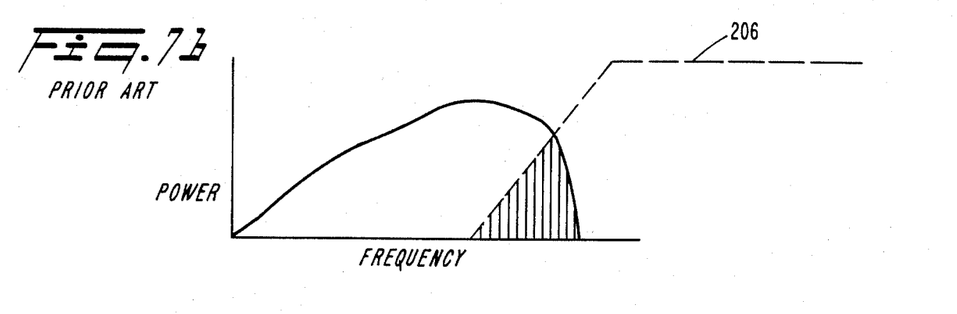

The shaded areas in FIGS. 6 and 7 are proportional to the feedback voltage. This voltage is also used as a measure of the frequency of the leading edge. In the ideal case, the area would vary linearly with the frequency of the leading edge on the X axis. It will be apparent that the ideal case is better approximated by the relatively steep slope of the filter characteristics in FIGS. 6a and b than by the less steep slope of the filter characteristics 206 of the prior art shown in FIG. 7a and b. As the spectrum increases in frequency, the VCO compensates by decreasing its output frequency thereby keeping the energy integral of the spectrum and filter at a fairly constant level. The steepness of the leading edge of the filter characteristic minimizes the error which might otherwise occur because of the fact that the higher the peak frequency of the spectrum, the greater the overlap between the spectrum and filter characteristic necessary to produce the required error voltage. This difference is minimized and, therefore, the linearity is improved with the steep filter. This may be contrasted to the prior art systems such as that shown by Calicott and Lunt which employ an audio frequency VCO signal and filters with necessarily lower Qs.

The tracking circuit complements the operation of the AGC circuit, in that the 440 Hz signal summed at circuit 108 sets the maximum gain of the AGC circuit so that when the Doppler signal amplitude is very low, the AGC gain does not increase to the maximum and thereby amplify noise. The signal emerging from the AGC circuit at A is such that the peak velocity tracking loop need track only frequency changes and not amplitude changes in the Doppler spectrum.

With continued reference to FIG. 9, the halfwave rectifier-peak follower circuit 124 may include a differential amplifier 126 and a feedback loop including Shottkey diodes 128 which perform a half-way rectification function. The signal appearing at node 130 is employed as a feedback signal for controlling the VCO 114 and also as a signal representative in value of the leading edge of the Doppler shift frequency spectrum. The loop circuit of the frequency tracking circuit 110 has an intrinsic gain which can be expressed numerically in terms of amplification divided by Hertz. In other words, the signal emerging from the peak follower at node 116 has a dc voltage value. For each increase in that dc voltage there is a corresponding increase in units of frequency in the output of the VCO 114. This quantity may be referred to as the "tracking system gain function." It has been found that a desirable value of the tracking system gain function for the preferred bandpass ceramic filter device is 12.5 kHz per volt DC. Higher values of tracking system gain function tend to lead to instability. Lower values of the tracking system gain function do not optimize the fidelity of tracking achievable with the circuit disclosed.

With continued reference to FIGS. 4 and 9, further signal processing circuitry will be described. The tracking signal appearing at node 130 may be applied to level adjust circuitry 140 employed to calibrate the system. The level adjusted signal is then applied to two clock controlled filters 142 and 144 whose filter characteristics are dictated by a clock circuit 146. The filters 142 and 144 are adjustable low-pass filters which smooth the output of the peak velocity tracking circuit without removing important velocity and acceleration information. Clock noise introduced into the signal may be removed by a clock noise filter 148.

The output signal of the clock noise filter 148, appearing at node 150 is representative in value of the peak Doppler frequency component. This signal may be differentiated by an operational amplifier differentiator 152. The differentiated signal, appearing at node 154 is representative of peak instantaneous acceleration.

Both the peak instantaneous velocity and peak instantaneous acceleration signals may be fed to peak detector circuits [not shown] which detect and hold the peak values of the signals observed at nodes 156 and 158, respectively. A calibrated visual display may be provided that directly shows peak velocity and peak acceleration in convenient units in real time such as in meters per second and meters per second$^2$. Alternatively, the successive peak velocity and acceleration measurements can be recorded for later reference.

Figure 10:
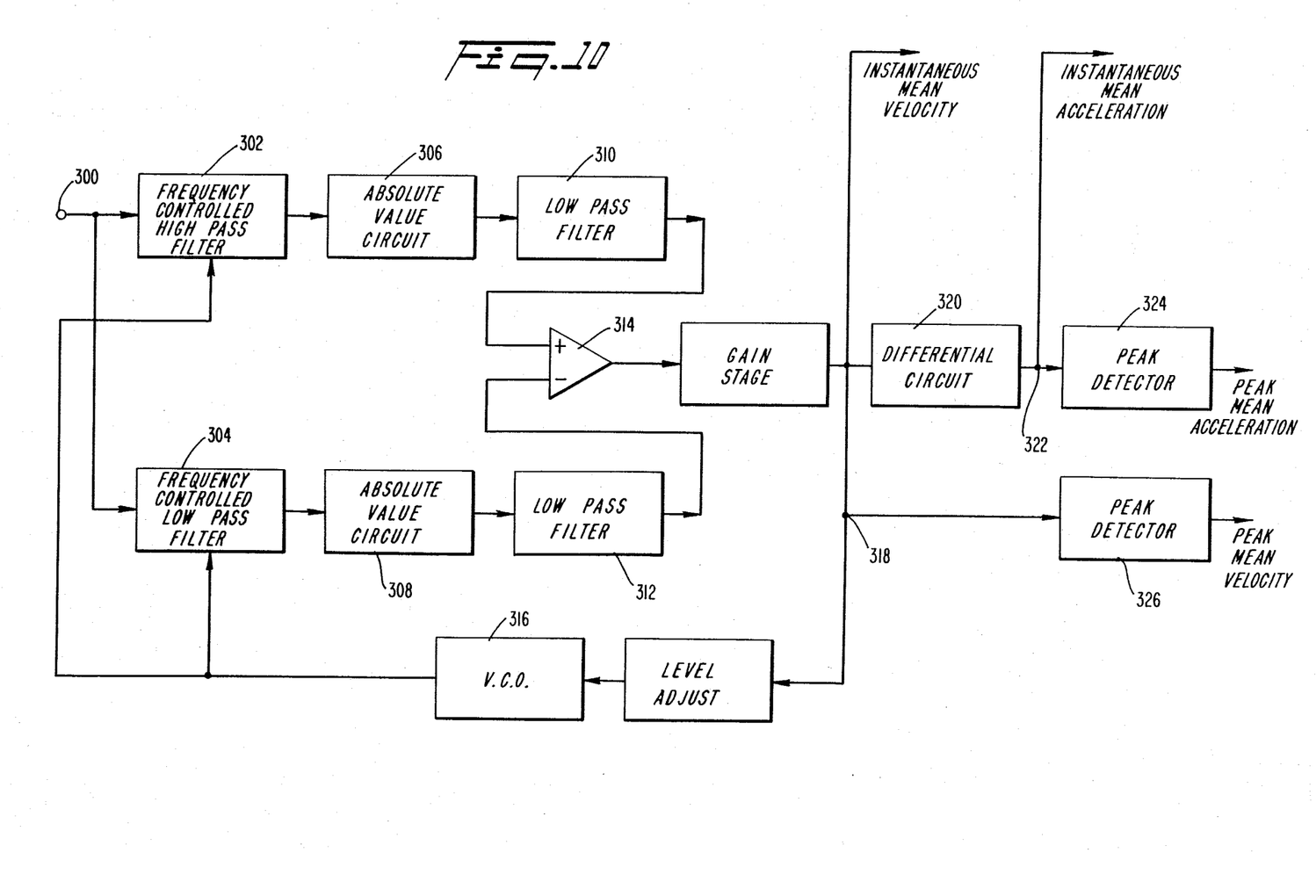
FIG. 10 is a schematic block diagram of a circuit for determining mean velocity and acceleration from a Doppler shifted ultrasonic signal.

Another embodiment of the present invention is illustrated in FIG. 10. A gain controlled Doppler shift signal from node A of FIG. 4 may be applied to the input terminal 300 of the circuit shown in block diagrammatic form in FIG. 10. The circuit of FIG. 10 operates on this signal to provide mean blood velocity and mean acceleration measurements. The circuit of FIG. 10 employs a parallel pair of frequency controlled filters; one, a high pass filter 302, the other, a low pass filter 304. In a preferred embodiment, both filters are operated so as to have the same cut off frequency. In the preferred embodiment the voltage controlled high pass and low pass filters may be built around a monolithic capacitor filter device known by the manufacturers designation MF10, manufactured by National Semiconductor, Inc.

The high pass filter 302 should, advantageously, roll off steeply at approximately the maximum Doppler frequency anticipated [12 khz] in order to avoid introducing error by integrating noise above that frequency. An absolute value of the signal passed by the high and low pass filters may be obtained by the absolute value circuits 306 and 308, which may be constructed in the same manner as the absolute value circuits described in connection with FIG. 9. Output signals of the absolute value circuits may then be filtered by low pass filters 310 and 312 respectively.

A difference in signal is produced by the differential amplifier 314. An output difference signal from the differential amplifier 314 is used to control a voltage controlled oscillator 116. A variable frequency signal from the voltage control oscillator is returned via a feedback loop to control the cutoff frequencies of the two voltage controlled filters 302 and 304.

Figure 11:
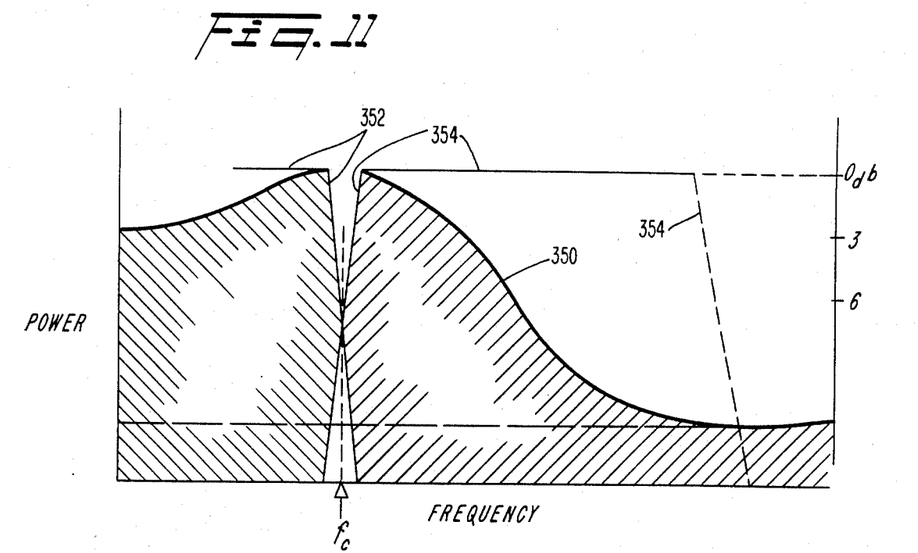
FIG. 11 is a graph of the spectrum of a Doppler shifted ultrasonic signal showing low and high filter cut off profiles useful in the circuit of FIG. 10.

The operation of the feedback loop is best described in connection with FIG. 11. In FIG. 11 the envelope of the frequency spectrum 350 of a Doppler shifted signal is plotted. Lines 352 represents the cut-off frequency profile of the voltage controlled low pass filter 304. Similarly, lines 354 represent the cut off frequency profile of the voltage controlled high pass filter 302. The feedback loop in FIG. 10 including the voltage controlled oscillator 316 operates so that the area under the curve 350 and within the low pass filter profile 352 is approximately equal to the area under curve 350 and within the high pass filter profile 354. It will be appreciated that the cut off frequency $f_c$ of the subsystem will move back and forth along the X axis of FIG. 11 as the Doppler shift signal varies during the heartbeat. It will also be appreciated that the cut off frequency $f_c$ corresponds approximately to the mean shifted frequency in the Doppler shifted signal. This in turn corresponds to the mean velocity of the reflecting blood components measured by the system.

The signal produced at node 318 is representative in value of the instantaneous mean velocity of the reflective components of blood. This signal may, in turn, be time differentiated by the differentiator circuit 320 to produce a signal at node 322 which is representative in value of the instantaneous mean acceleration of the blood. Finally, peak detectors 324 and 326 may be employed which detect the peak mean acceleration and peak mean velocity of the blood during a single heartbeat. As with the previous embodiments these signals may be applied to suitable recording or displaying apparatus.

Figure 12:
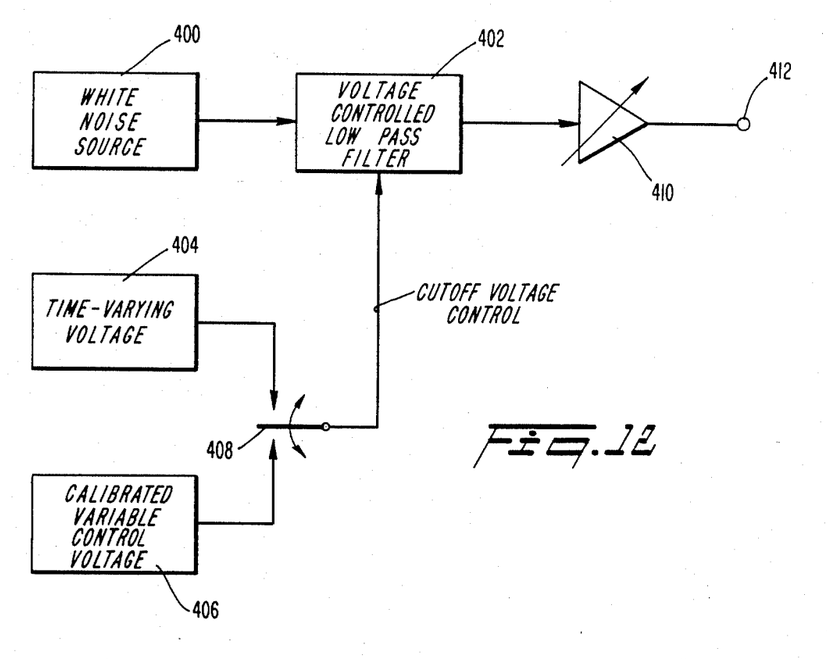
FIG. 12 is a schematic block diagram for a circuit useful in calibrating blood flow measurement devices.

FIG. 12 is a schematic block diagram of a calibration circuit suitable for use with embodiments of the present invention discussed above. The calibration circuit consists of a white noise source 400, the energy output of which may be approximately flat from D.C. to 20 KHz. This output signal is fed to a voltage controlled low pass filter 402, the cutoff frequency of which can be varied from 100 Hz to 20 KHz. The filter cutoff frequency can be controlled by a time-varying voltage source 404 or a calibrated variable control voltage 406. The selection of control voltages may be accomplished by means of a mechanical switch 408. A filtered signal from the filter 402 may be applied to a variable gain amplifier 410. An output signal at terminal 412 of the amplifier 410 may be applied as a calibration signal to the blood velocity and acceleration measurement circuits described above.

The output signal of the calibration circuit is a band limited white noise signal which simulates the instantaneous Doppler spectrum produced by blood motion in the aorta. A known spectrum of constant amplitude and frequency distribution is produced when the calibrated control voltage is used. In contrast, varying spectra are produced by the circuit when it is controlled by the time-varying voltage. Such spectra simulate the time varying spectra characteristic of heart beats.

The measurement of blood motion can be calibrated by employing the band limited white noise signal with a known cutoff frequency from the calibration circuit in place of said audio frequency Doppler shift signal and adjusting the system output signal (normally representative of a blood flow parameter) in accordance with a known calibration value associated with the band limited white noise signal.

Although the invention has been described in connection with preferred embodiments, it is to be understood that variations and modifications may be resorted to as will be apparent to those skilled in the art. Such variations and modifications are to be considered within the purview and the scope of the claims appended hereto.

I claim:

1. An apparatus for measuring instantaneous peak velocity in blood flow through a blood vessel, comprising
    means for obtaining a Doppler signal having a frequency spectrum determined by Doppler shifting of an ultrasonic signal caused by relative movement of components of the blood in the blood vessel; and
    means for tracking a high frequency edge of said frequency spectrum to produce a signal representative in value to the instantaneous peak velocity of the blood components, said tracking means including means for modulating said Doppler signal up to a frequency above 100 kHz.

2. The apparatus of claim 1 wherein said Doppler signal obtaining means comprises:
    transducer means for directing ultrasonic energy at blood flowing in a blood vessel and for receiving ultrasonic energy reflected by blood components flowing in the blood vessel; and
    means for electronically extracting audio frequency Doppler shift signals from the reflected and received ultrasonic energy.

3. The apparatus of claim 2 wherein said modulating means comprises:
    controllable oscillator means for producing a signal having a frequency greater than 100 kHz;
    means for mixing the audio frequency Doppler shift signals with the oscillator means signal to thereby modulate the Doppler signal up to a frequency above 100 kHz;
    wherein said tracking means further comprises a fixed, band pass filter means for filtering the mixed signal; and
    wherein the oscillator means is controlled so that a portion of the mixed signal, corresponding to a high frequency edge of the spectrum of the Doppler shift signal, is maintained in the pass band of the filter.

4. The apparatus of claim 3 wherein the band pass filter means is a ceramic filter with fixed band pass characteristics.

5. The apparatus of claim 3 wherein the band pass filter means has a Q greater than 100.

6. The apparatus of claim 3 wherein the audio frequency Doppler shift signals from the extracting means are band limited to between about 100 Hz and 10,000 Hz.

7. The apparatus of claim 1 further comprising means for differentiating said signal representative in value to the instantaneous peak velocity of the blood components to produce a signal representative in value to the instantaneous peak acceleration of the blood flow.

8. The apparatus of claim 1 further comprising an automatic gain control circuit for normalizing the power in the frequency spectrum of said Doppler signal during the heart beat while preserving the frequency distribution in the spectrum, including
    a source of a sinusoidal signal having a frequency lower than about 1000 Hz; and
    means for summing the Doppler signal and the sinusoidal signal and for maintaining approximately constant the peak to peak amplitude of the summed signal;

said gain controlled signal being applied to the tracking means.

9. A method for measuring instantaneous peak acceleration in blood flow through a blood vessel, comprising the steps of:
(a) directing ultrasonic energy at blood flowing in the blood vessel;
(b) receiving ultrasonic energy reflected by blood components flowing in the blood vessel;
(c) electronically extracting audio frequency Doppler shift signals from the reflected and received ultrasonic energy;
(d) mixing the audio frequency Doppler shift signal with a signal having a frequency greater than 100 kHz generated by a local oscillator;
(e) filtering the mixed signal;
(f) controlling the local oscillator responsive to said filtered signal to vary the frequency of the local oscillator signal so that a portion of a side band of the mixed signal, corresponding to a high frequency edge of the spectrum of the Doppler shift signal, is maintained in a pass band of the filter; and
(g) differentiating with respect to time the filtered signal to produce a signal representative in value to the instantaneous peak acceleration of the blood flow.

10. The method of claim 9 further comprising the step of calibrating the measurement of instantaneous peak acceleration in blood flow by employing a band limited white noise signal with a known cut-off frequency in place of said audio frequency Doppler shift signal and adjusting the signal representative in value of blood acceleration in accordance with a known calibration value associated with said band limited white noise signal.

11. An apparatus for noninvasively measuring blood flow in a blood vessel comprising:
ultrasonic probing means for obtaining a Doppler signal caused by Doppler shifting due to reflection of ultrasonic energy from moving components of the blood in the blood vessel including means for demodulating the Doppler signal to produce an audio frequency Doppler signal; and
means for receiving said audio frequency Doppler signal and for producing a signal representative in value to the instantaneous peak velocity of the blood components including modulation means employing a local oscillator producing a signal of a frequency greater than 100 kHz.

12. An apparatus for measuring blood flow through a blood vessel comprising:
means for obtaining a Doppler signal produced by Doppler shifting of an ultrasonic signal by reflection from moving blood in the blood vessel;
an automatic gain control circuit for receiving said Dopper signal and for normalizing the power in the frequency spectrum of said Doppler signal during the heart beat while preserving the frequency distribution in the spectrum, including means for summing the Doppler signal with a sinusoidal signal having a frequency lower than any Doppler frequency shift to be evaluated, and maintaining the peak to peak amplitude of the summed signal at an approximately constant value; and
means for tracking Doppler frequency shift in the Doppler signal as it varies during the heartbeat and producing a signal representative in value of a blood flow parameter.

13. The apparatus of claim 12 wherein said signal producing means includes means for producing a signal representative in value of instantaneous peak velocity.

14. The apparatus of claim 12 further comprising means for differentiating the peak velocity signal with respect to time to provide a signal representative of the instantaneous peak acceleration of the blood.

15. The apparatus of claim 12 wherein said signal producing means includes means for producing a signal representative in value of instantaneous mean velocity of reflecting blood components.

16. The apparatus of claim 15 further comprising means for differentiating the velocity signal with respect to time to provide a signal representative in value of the mean acceleration of the reflecting blood components.

17. A method for measuring blood flow through a blood vessel, comprising the steps of:
obtaining a Doppler signal produced by Doppler shifting of an ultrasonic signal by reflection from moving blood in the blood vessel;
summing the Doppler signal with a continuous sinusoidal signal having a frequency less than about 1000 Hz;
electronically maintaining said summed signal at an approximately constant amplitude during the heart beat; and
electronically tracking frequency components of the approximately constant amplitude signal to produce a signal representative in value of the velocity of the blood.

18. The method of claim 17, wherein said tracking is performed by heterodying the approximately constant amplitude signal with a signal having a frequency above 100 kHz.

19. The method of claim 17, wherein the sinusoidal signal has a frequency above the frequency of sounds produced by the heart beat.

20. The method of claim 19, wherein the sinusoidal signal has a frequency from 100 to 1000 Hz.

21. The method of claim 17, wherein the step of electronically tracking frequency components include the determining of the instantaneous mean velocity of the reflecting blood components by applying the approximately constant amplitude signal to first and second electronically controlled filters arranged in parallel, said first filter passing relatively higher frequency components of the Doppler signal and said second filter passing relatively lower frequency components, said filters being controlled by a feedback control signal so that the power in the portion of the Doppler signals passed by each is maintained approximately equal, the instantaneous mean velocity being determined from the feedback control signal.

22. An apparatus for measuring the mean velocity of blood flowing in a blood vessel comprising:
transducer means for producing ultrasonic energy directed at blood flowing in the blood vessel;
means for receiving ultrasonic reflected by blood components flowing in the blood vessel and for electronically extracting audio frequency Doppler shift signals from the reflected and received ultrasonic energy;
a first electronically controlled filter;
a second electronically controlled filter, wherein the Doppler shift signal is applied to each of the electronically controlled filters and wherein said filters selectively pass different portions of the audio frequency spectrum of the Doppler shift signal;

feedback circuit means for providing a signal for controlling the first and second filter so that the portion of the Doppler shift signal passed by each filter maintain a predetermined relationship to one another, said feedback signal being related in value to the instantaneous mean velocity of moving, reflecting components of the blood in the blood vessel.

23. The apparatus of claim 23 wherein the said audio frequency Doppler signal is band-limited and the spectrum of the band-limited signal is divided into a high pass portion and a low pass portion by the first and second filters, respectively.

24. The apparatus of claim 24 wherein the lower boundary frequency of the high pass portion is substantially equal to the upper boundary frequency of the low-pass portion.

25. The apparatus of claim 23 further comprising:

(a) circuit means for producing a signal responsive to an envelope of an absolute value of signal peaks in the signal passed by the first filter;
(b) circuit means for producing a signal responsive to an envelope of an absolute value of signal peaks in the signal passed by the second filter; and wherein said feedback circuit means includes means for differentially combining output signals of circuit means (a) and (b), and for producing said feedback control signal therefrom.

26. The apparatus of claim 26 further comprising means for differentiating the feedback control signal to obtain a signal related in value to the instantaneous mean acceleration of the reflection components of the blood.

27. The apparatus of claim 25 wherein the feedback circuit further comprising a voltage controlled oscillator and wherein said filters are monolithic and each are controlled responsive to a signal from the voltage controlled oscillator, the control signal for said oscillator being said feedback control signal.

* * * * *